(12) United States Patent  
Calderon

(10) Patent No.: US 7,914,514 B2
(45) Date of Patent: Mar. 29, 2011

(54) COMPUTERIZED SYSTEM FOR MONITORED RETROGRADE PERFUSION OF TUMOR SITES

(76) Inventor: Reynaldo Calderon, Houston, TX (US)

( * ) Notice: Subject to any disclaimer, the term of this patent is extended or adjusted under 35 U.S.C. 154(b) by 1064 days.

(21) Appl. No.: 11/154,413

(22) Filed: Jun. 16, 2005

(65) Prior Publication Data

US 2006/0149393 A1    Jul. 6, 2006

Related U.S. Application Data

(63) Continuation-in-part of application No. 11/026,103, filed on Dec. 30, 2004.

(51) Int. Cl.
*A61M 31/00* (2006.01)
(52) U.S. Cl. ........................................................ 604/509
(58) Field of Classification Search .................. 604/505, 604/500, 510, 507, 28, 35; 600/10
See application file for complete search history.

(56) References Cited

U.S. PATENT DOCUMENTS

| | | | |
|---|---|---|---|
| 4,714,460 A * | 12/1987 | Calderon | 604/28 |
| 4,867,742 A * | 9/1989 | Calderon | 604/28 |
| 4,883,459 A * | 11/1989 | Calderon | 604/28 |
| 5,011,469 A * | 4/1991 | Buckberg et al. | 604/6.11 |
| 5,040,540 A * | 8/1991 | Sackner | 600/485 |
| 5,190,045 A * | 3/1993 | Frazin | 600/463 |
| 5,220,924 A * | 6/1993 | Frazin | 600/468 |
| 5,423,743 A * | 6/1995 | Butterfield | 604/505 |
| 5,533,957 A * | 7/1996 | Aldea | 600/16 |
| 5,546,949 A * | 8/1996 | Frazin et al. | 600/439 |
| 5,597,377 A * | 1/1997 | Aldea | 600/16 |
| 5,740,808 A * | 4/1998 | Panescu et al. | 600/424 |
| 5,851,985 A * | 12/1998 | Tepic et al. | 514/2 |
| 6,485,489 B2 * | 11/2002 | Teirstein et al. | 606/41 |
| 2001/0023345 A1 * | 9/2001 | Wolff et al. | 604/500 |
| 2001/0041862 A1 * | 11/2001 | Glickman | 604/101.01 |
| 2001/0044598 A1 * | 11/2001 | Parodi | 604/104 |
| 2002/0115994 A1 * | 8/2002 | Teirstein et al. | 606/41 |
| 2003/0157024 A1 * | 8/2003 | Tachibana et al. | 424/9.52 |

* cited by examiner

*Primary Examiner* — Kevin C Sirmons
*Assistant Examiner* — Michael J Anderson
(74) *Attorney, Agent, or Firm* — Raymond R. Ferrera; Adams and Reese LLP

(57) ABSTRACT

A computerized system collects, organizes and stores various sets of data during several phases of treatment relating to monitoring and location of a route in vivo and a visible image of that route for retrograde perfusion of a tumor with a therapeutic agent and for monitoring treatment procedures during such retrograde perfusion. The data obtained from present and past treatment procedures are stored for analysis and also made available real time to treating physicians during treatment procedures.

20 Claims, 13 Drawing Sheets

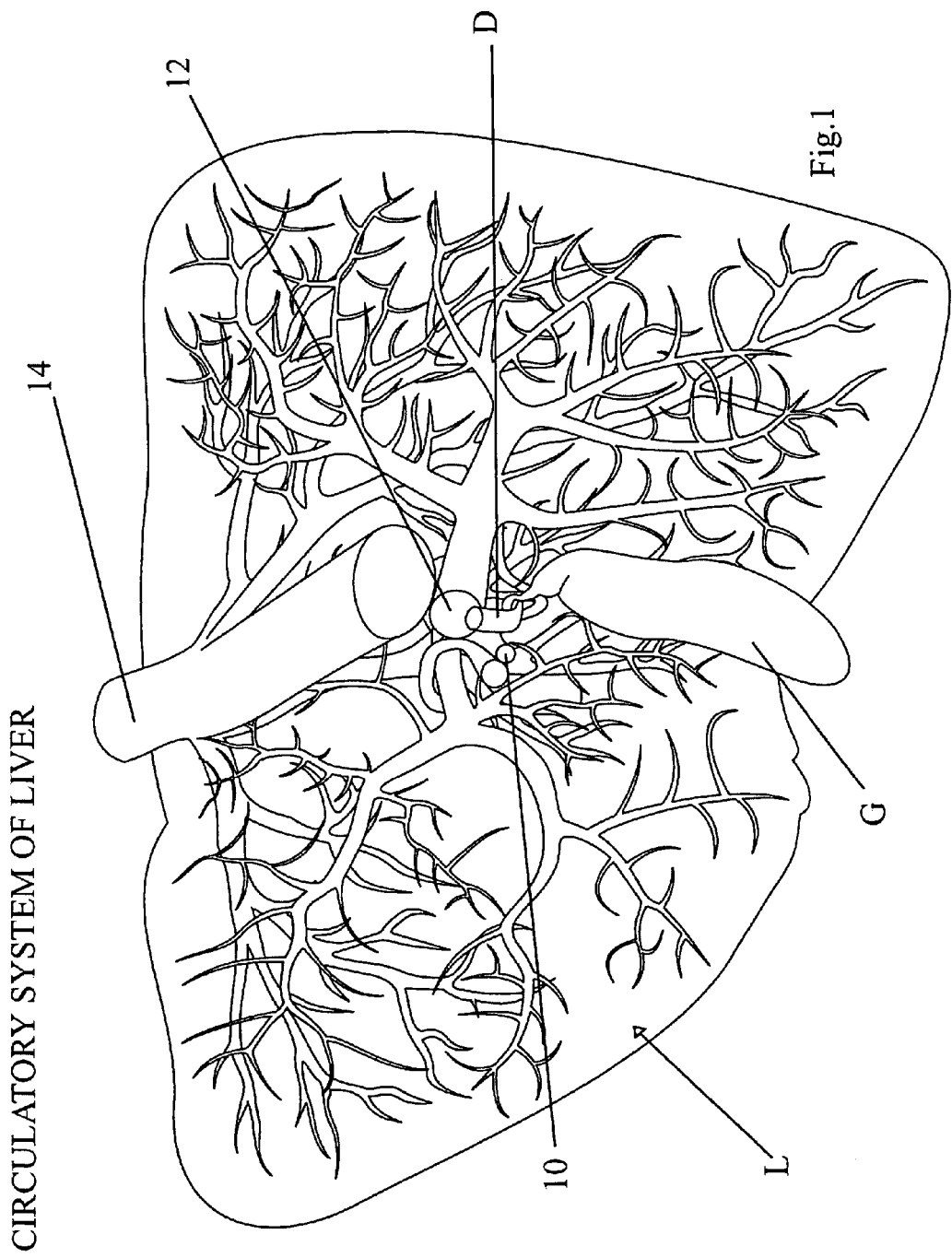

COMPUTERIZED SYSTEM FOR MONITORED RETROGRADE PERFUSION OF TUMOR SITES

CROSS-REFERENCE TO RELATED APPLICATION

The present application is a continuation-in-part of prior co-pending U.S. patent application Ser. No. 11/026,103 filed Dec. 30, 2004.

BACKGROUND OF THE INVENTION

1. Field of the Invention

The present invention relates to computerized methods and systems for monitoring delivery of therapy to organ sites and to tumor sites in particular. More specifically, the present invention provides an improved new and improved computerized systems and methods for obtaining, organizing, storing and presenting to treating physicians in real time data relating to retrograde perfusion. The retrograde perfusion may include, for example, delivery of chemotherapy, gene therapy or other therapeutic agents to diseased or cancerous sites, and particularly to solid tumors.

2. Description of the Related Art

U.S. Pat. Nos. 4,714,460, 4,867,742 and 4,883,459, of each of which Applicant is inventor, relate to methods and systems for study and treatment in situ of tumors in a subject patient's body of retrograde perfusion. Although the techniques of retrograde perfusion have been considered as possibly advantageous and helpful, there has been hesitancy to attempt widespread experimentation using the techniques of these patents. There are also several problems still remaining which have hampered attempts in this area for treatment of tumors, regardless of the method or system proposed.

There has been an uncertainty or blind spot in the delivery procedure with respect to the path of travel or trajectory that a therapeutic agent travels during the infusion or treatment procedure. This has in turn caused a resultant unpredictability regarding the route(s) taken by a therapeutic agent once the agent has been administered by conventional intravenous delivery techniques.

Another problem has involved inadequate uptakes and nonoptimal distribution in tumors in vivo. As has been pointed out in Applicant's earlier U.S. Patents: The tumor blood flow is thus impaired, measuring only two to fifteen percent of that of the surrounding tissue, and this impaired circulation distinguishes the cancer vasculature. The probability of blood flow through the V-V shunts is far less than the probability of blood flow through the normal vasculature. Therefore, in any attempt to deliver chemotherapy to a tumor, the likelihood that the drug will spread to the remainder of the body is far greater than the likelihood that it will reach the tumor. There were problems in making certain that the tumor (rather than the entire body) received a significantly high dose and duration of exposure to the treatment agent. Another problem was in determining and controlling the routes of drug delivery within a target site, as well as that of withdrawing any excess drug.

Dynamic fluoroscopic maps enabled a physician to somewhat visualize at a macroscopic level delivery routes and a target site. However, the fluoroscopic images that captured macroscopic data were incapable of tracking the flow dynamics at the submicroscopic level of cellular activity.

Another problem has been isolation of the treatment agent to the area of the tumor in the patient. Avoiding systemic leakage of toxic drugs that cause damage to healthy tissue and organs has been a major problem in the delivery of chemotherapy. Obtaining precise delivery of genetic material to a target region has continued to be a desirable goal of gene therapy. Regardless of the agent being delivered, localized, precise, targeted therapy delivery to a specific site with negligible run-off or leakage of the agent to collateral sites has remained a concern.

There are certain agents which have proven effective in chemotherapeutic treatment of tumors, but which have potentially severe side effects. An example is doxorubicin, available under the trademark ADRIAMYCIN®, which has been used as an anti-cancer drug for a number of years. That composition has been used to treat many forms of cancer including cancer of the breast and stomach, lymphoma and multiple myeloma. However, severe side effects have ensued. A common side effect if dosage is not controlled has been dilated cardiomyopathy. The use of this chemical to treat tumors has been limited, when systemically administered, due to its toxic side effect on the patient's heart.

SUMMARY OF THE INVENTION

Briefly, the present invention provides a new and improved computer-implemented method of monitoring retrograde venous perfusion of a tumor in a patient's body According to the method of the present invention, the positioning is monitored of a withdrawal catheter within vasculature of a target vessel in the patient's body near the tumor, and of an infusion catheter within the vasculature of the target vessel near the tumor and beyond the withdrawal catheter. The positioning of a venous pressure catheter within the vasculature of the target vessel and intermediate the infusion catheter and the withdrawal catheter is also monitored. The location and positioning which are monitored allow observation of a closed loop flow path between the positioned infusion catheter and the positioned withdrawal catheter through the target vessel. Venous pressure is monitored in the closed loop flow path, and the circulation of fluids through the closed loop flow path is also monitored.

The process of the present invention allows control of the delivery of therapy via the retrograde perfusion modality. It provides for monitoring and presentation of a multitude of complex and continually changing variables during the tumor treatment by retrograde perfusion.

The present invention also provides a computerized system for monitoring the retrograde perfusion of tumors. A processor of the computer system performs the steps of the computer implemented monitoring of the retrograde perfusion of the tumor. The present invention also provides a computer program product containing machine-readable code that causes the processor to implement the monitoring of the retrograde perfusion. By virtue of the position of the catheters relative to one another and to the target vessel, the treating physician is provided with monitoring capability to verify that the perfusion treatment is carefully controlled and monitored, and that the flow of fluids in the vasculature and tumor region is in accordance with fluid dynamic and flow principles.

There is, however, no need to establish or define specific fluid flow equations of motion explicitly in order to verify that proper perfusion fluid flow paths and relations are established and maintained. The control or treatment unit when positioned and monitored with the present invention during its use and operation implicitly computes the solution to the equations of motion for the network, and performs the perfusion treatment according to the desired flow paths and relationships. This is done without resorting to the explicit use of calculations, numbers, mathematical equations or physical equations of motion and such; proper positioning of the control unit during its use performs those kinds of computational tasks.

Recognizing that timely intervention and response is a critical factor in the management of disease processes, the present invention makes it possible to synchronize the multiple disparate signals related to any one or more of a number of factors of interest during retrograde perfusion on a real-time basis. Data or images of interest include:

(1) the catheter, i.e. infusion rate, withdrawal rate, fluid displacement, pressure, concentration;
(2) the patient's history and present condition, i.e. prior surgeries and treatments, current heart rate, blood pressure, respiration, temperature;
(3) 3-D high resolution imaging, i.e. spatial boundaries, borders, density; and
(4) ongoing response to therapy at the cellular level.

The present invention is capable of putting these disparate signals in a synchronized or zero-state of image retention in a manner that, so far as is known, has not been previously contemplated. In addition to providing a high degree of control and integration to the treatment process, the present invention offers a treating physician with up-to-the-minute support for planning, decision-making, and problem-solving.

All data including three-dimensional or 3-D models are data archived in a central repository so that data mining, predictive modeling, and suggested action states may be applied to various systems. Local systems can be networked to remote systems so that data available at a treatment center in one locality is simultaneously available to treatment centers in other localities.

Two examples or models help to explain by analogy the kinds of differential equations of motion that are implicitly solved by operation of the control unit. One is a water-flow model that cascades; the other is a moving crowd model. In the water-flow model, the size and shape of the catheters influence the motion of fluid through the catheters. Also, the motion of fluid in parallel and opposite directions, and orientation through the catheters and through the vascular beds obeys the physical laws related to pressure, flow rate, and volume. In the moving crowd model, the size and shape of the catheters influence the movement of particles through the catheters. Also, the movement of particles through the network conforms to the physical laws related to pressure, flow rate, and volume.

BRIEF DESCRIPTION OF THE DRAWINGS

A better understanding of the present invention can be obtained when the detailed description set forth below is reviewed in conjunction with the accompanying drawings, in which:

FIG. 1 is photograph of a highly simplified model of the circulatory system in the liver of an animal.

DETAILED DESCRIPTION OF THE PREFERRED EMBODIMENTS

Figure 2A:
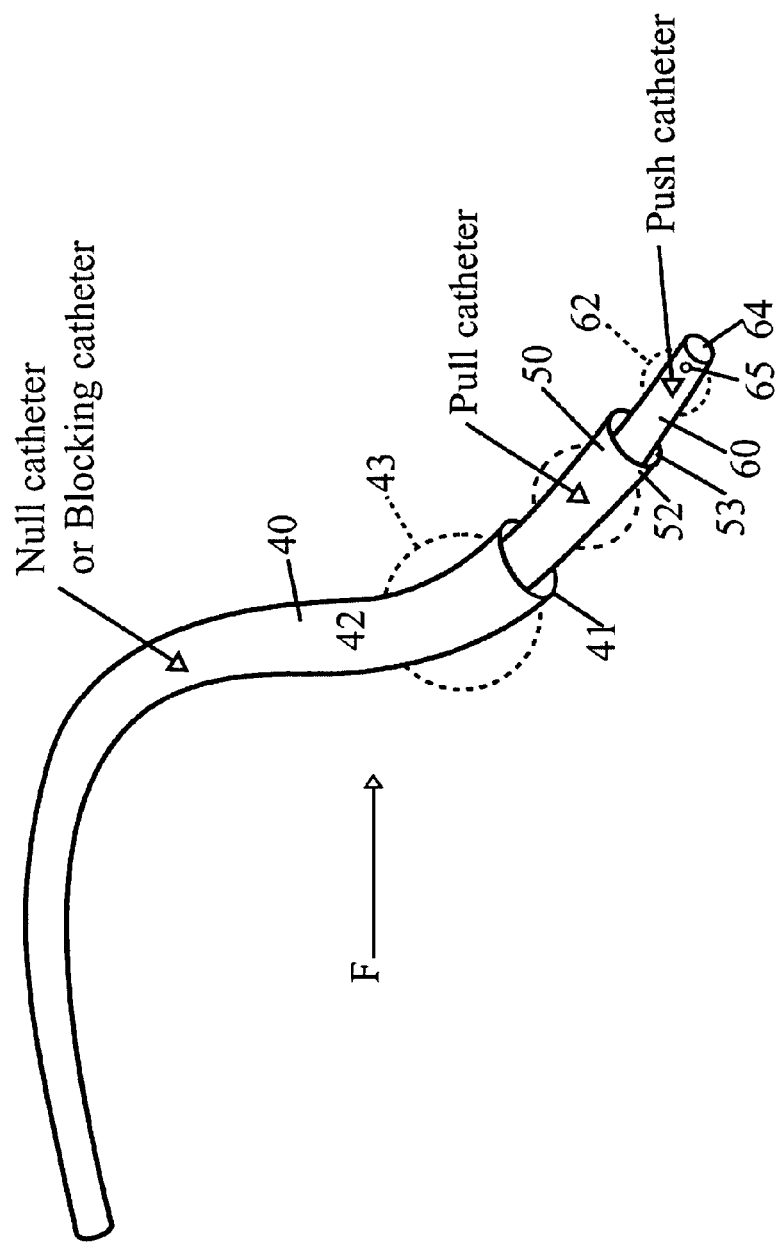
FIGS. 2A and 2B are isometric views of catheter system portions of the present invention.

In the drawings, a photographic model of the circulatory system of blood flow the liver of an animal, in this case a human, is shown in FIG. 1. The liver L is located in the body in communication through the common bile duct D with the gallbladder G. As indicated at 10, the hepatic artery connects to and transports blood into the liver L for the purpose of bile production, protein production, blood detoxification and other liver functions.

In the treatment of tumors in other organs, a similar approach applies. In the case of a tumor of the kidney, for example, the renal artery carries blood from the aorta to the kidney while the renal vein carries blood from the kidney to the inferior vena cava. For the purpose of retrograde perfusion, access to a tumor of the kidney would be via the inferior vena cava to the renal vein.

Further, retrograde perfusion can also be performed via percutaneous access to any organ whereby the venous drainage of the target organ is accessed directly via an incision. In any given organ, the point of reference for the process of retrograde perfusion is the site of the venous drainage from the organ.

The other major blood flow paths in the liver in addition to the hepatic artery 10 are also indicated in FIG. 1, including the portal vein as indicated at 12 and the inferior vena cava as indicated at 14. Blood enters the liver L from the heart via the hepatic artery 10 and from the stomach, intestines and other parts of the digestive tract through the portal vein 12.

Figure 5:
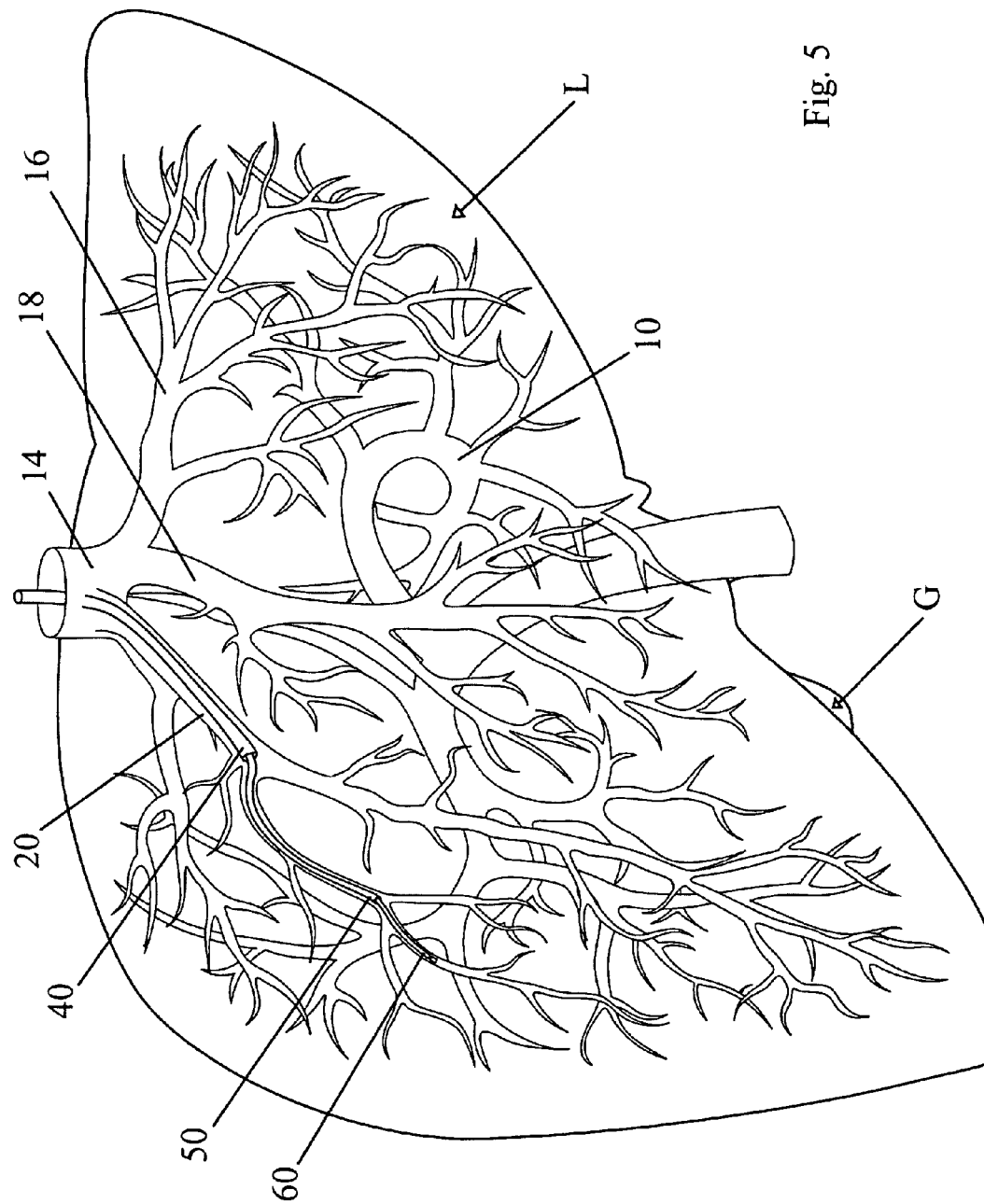
FIG. 5 is a schematic drawing of a liver receiving treatment during a procedure with a perfusion system of the present invention.
Figure 6:
FIG. 6 is a photograph of a model like that of FIG. 1 with a catheter according to FIG. 2A.

Incoming blood from the hepatic artery 10 and portal vein 12 merges and passes through the liver L to a series of hepatic veins (FIG. 5), including the left hepatic vein 16, a middle hepatic vein 18 and a right hepatic vein 20. The hepatic veins 16, 18 and 20 collect blood as it is processed in the liver L and empty into the inferior vena cava 14. As can be seen in FIG. 1, the hepatic artery 10 and the veins 12, 16, 18 and 20 are only the major blood flow paths through the liver L. There are as indicated in FIG. 1 a considerable number of other separate and distinct smaller or minor blood flow paths or veins branching off and in flow communication with the major flow paths. Because of the number of them, no reference indicators are assigned them in FIG. 1.

Such branching structures are examples of fractal architecture found commonly in a wide variety of physiological systems including the respiratory, circulatory, and nervous systems. Examples of fractal anatomy can be seen in anatomical structures such as the hepatic arterial and venous trees shown in FIG. 1.

As opposed to classical geometric forms that are smooth and regular having integer dimensions such as one, two and three for line, surface, and volume, fractals have a fractional dimension between one and two and exhibit a pattern of repeating smaller scale sub-patterns that resemble the larger scale pattern, a property terms self-similarity or scale invariance. Such fractal scaling is seen in the lungs, the bronchial tubes, capillaries, intestinal lining, and bile ducts; and the heart comprises various fractal networks including the coronary arteries and veins, the fibers binding the valves to the heart wall, the cardiac muscles themselves, and the His-Purkinje system that transmits electrical impulses from atrium to ventricle.

Fractal structures exhibit another significant property, the relationship between perimeter and area. A physiologic advantage of self-similar fractal structures is that they serve a common physiological function that has been characterized in the literature as "rapid and efficient transport over a complex, spatially distributed system. In the case of the ventricular electrical conduction system, the quantity transported is the electrical stimulus regulating the timing of the cardiac contraction. For the vasculature, fractal branchings provide a rich, redundant network for distribution of $O_2$ and nutrients and for the collection of $CO_2$ and other metabolic waste products. A variety of other organ systems contain fractal structures that serve functions related to information distribution (nervous system), nutrient absorption (bowel), as well as collection and transport (biliary duct system, renal calyces). "Nonlinear Dynamics, Fractals and Chaos Theory: Implications for Neuroautonomic Heart Rate Control in Health Disease", Ary L. Goldberger, 6-8.

Further, the model liver L of FIG. 1 although seemingly detailed is instead conceptual in that only a certain number of even the minor blood flow paths are represented, due to limits on the ability to form tangible representations of a number of the minor flow paths. The liver as in the case of other body organs or regions has in actuality a number of other smaller blood veins and flow paths, which are hard to discern and visualize. Further, the circulatory system embodied in the model of the liver L is a tangible, physical manifestation of the blood flow paths at a fixed moment.

Similar blood flow structure exists in other body organs as well. Accordingly, the liver as illustrated in FIG. 1 is given by way of example. It should be understood that the perfusion techniques of the present invention to be described below are equally applicable to other organs and portions of the body.

In the human or other animals, the flow of blood in flow paths through an organ such as the liver fluctuates in both pressure and flow rate in response to heart rate and blood pressure. As a result when an organ under investigation is viewed through body imaging systems as a display image by a treating physician, the organ appears much like a cloud or blurred image. Thus, in treating an organ, the display images are less articulated and defined in the body than the idealized, simplified flow path models as illustrated in the photograph of FIG. 1.

As mentioned above, it is known that there are chemotherapeutic agents of demonstrated effectiveness in treatment of tumors. However, their use has been significantly limited by the undesirable side effect of systemic toxicity on other organs or parts of the body. Although earlier retrograde perfusion efforts, as exemplified in Applicant's United States Patents mentioned above, have shown promise, certainty of the localization and isolation of the area of the patient's body receiving a chemotherapeutic agent is still a desirable goal. This holds true for chemotherapeutic agents of any type, but particularly those with undesirable systemic side effects, whether toxicity or some other undesirable effect.

Figure 3:
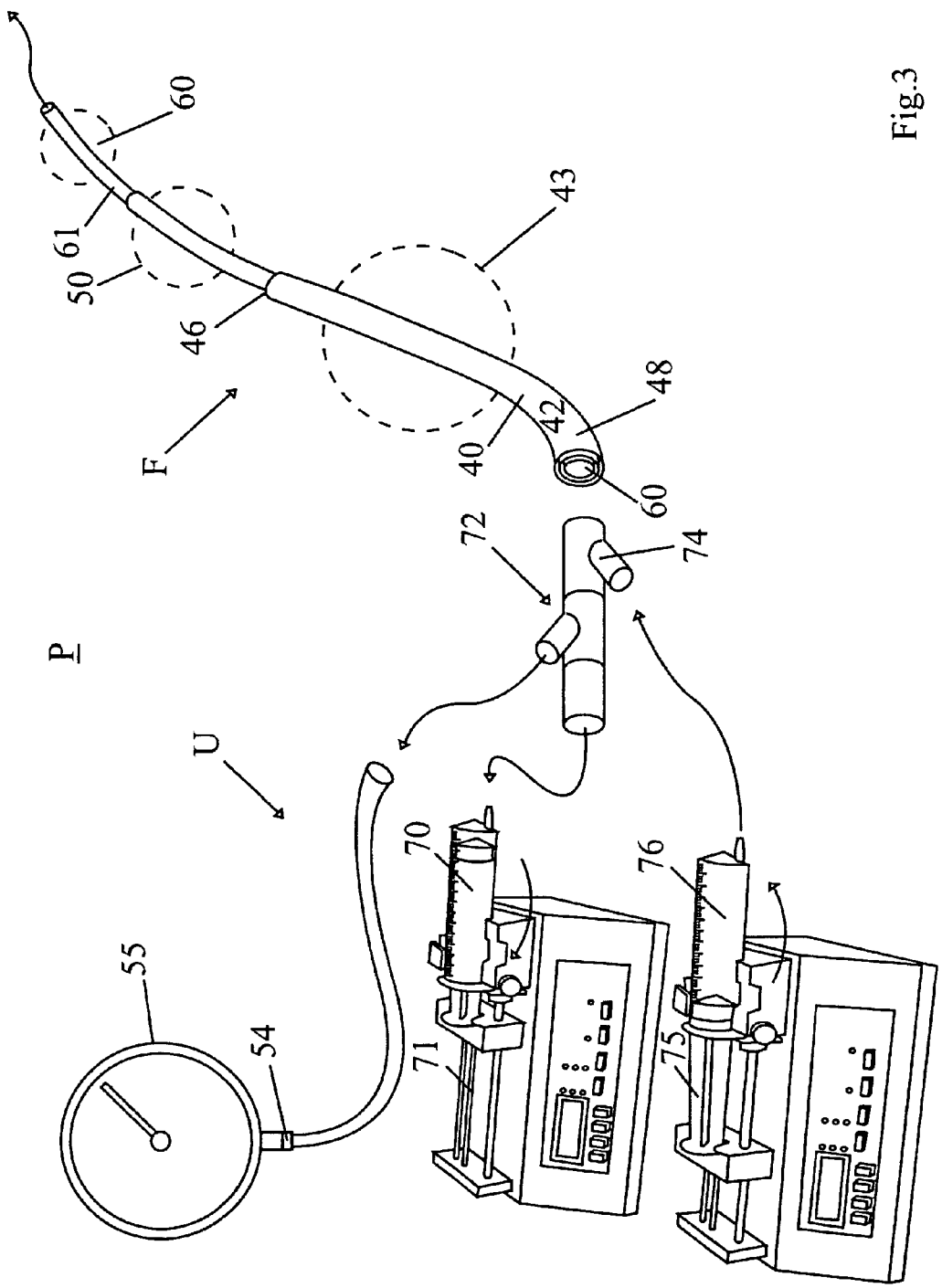
FIG. 3 is a schematic diagram of a perfusion system according to the present invention.
Figure 4:
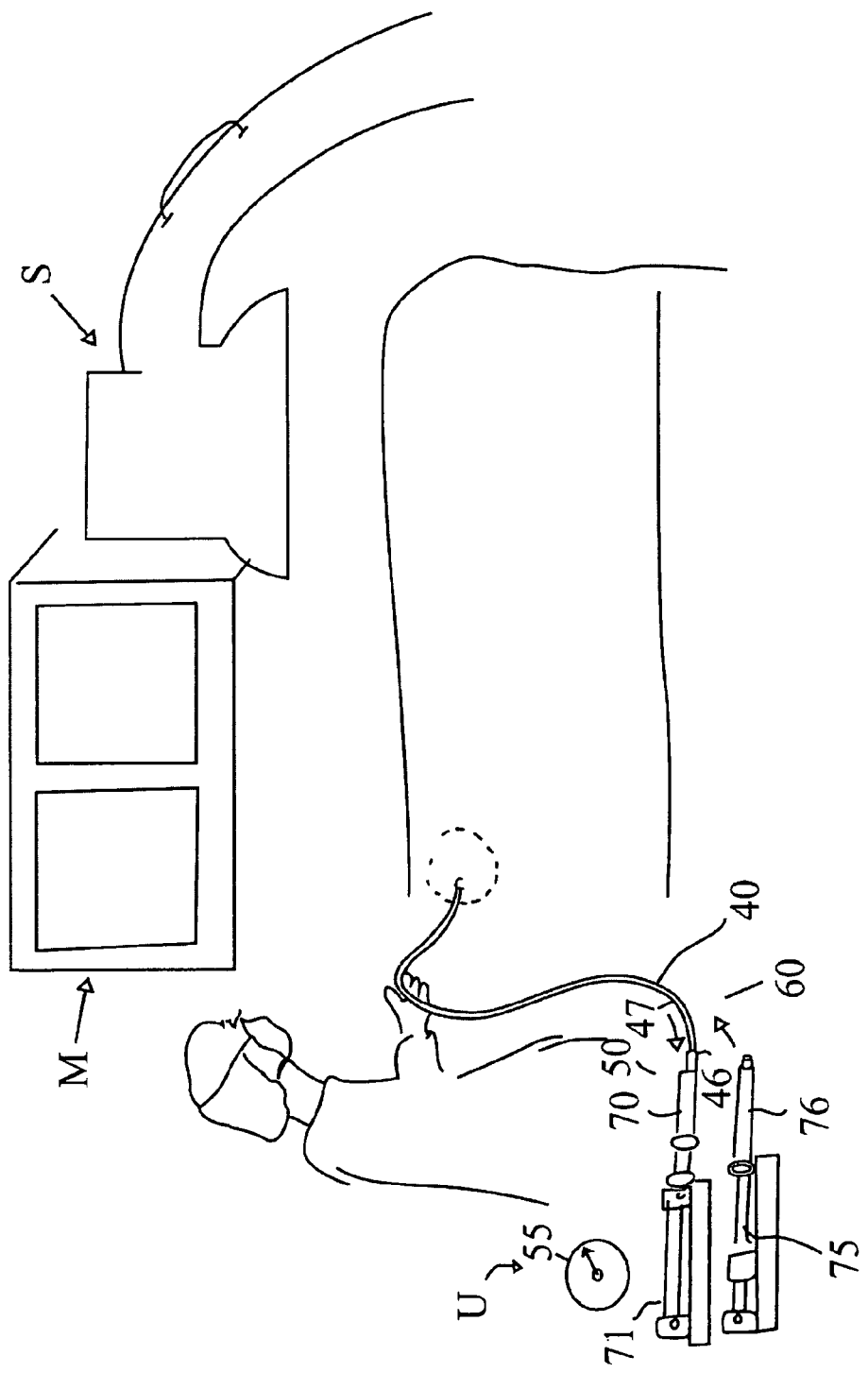
FIG. 4 is a schematic diagram of a treatment procedure with the perfusion system of FIG. 3.

The present invention provides a method and apparatus for retrograde perfusion of a patient with a therapeutic agent in a flow, controlled, pressure regulated in vivo closed loop in the vasculature of the patient. The apparatus of the present invention takes the form of a retrograde perfusion system P that includes a flow control or administration unit F (FIGS. 2A and 2B) that is introduced into the body of the patient. The flow control unit F is in fluid communication with an external unit U (FIGS. 3 and 4) with monitors and pumps with which treating physicians and their staff may administer the therapeutic agent, even one with substantial system toxicity, by retrograde perfusion in a closed loop, pressure regulated flow route in vivo. Typically, one or more visual monitors M are provides to display images formed for example by fluoroscopy or by computerized axial tomography or CAT scanner S. The monitors M allow the treating physician or physicians to gain visible confirmation of the formation, establishment and operation of the in vivo flow route.

The internal flow control unit F is a multicatheter system introduced into the vascular system of the patient at a suitable location, for example by femoral or neck cutdown, depending on the organ or portion of the patient's body to receive the therapeutic agent. The flow control unit F includes three catheters that may be configured to be concentrically mounted with each other (FIG. 2A) or may have two of the catheters separately contained (FIG. 2B) within a third or larger outer catheter.

In a flow control unit 30 according to the present invention, a larger catheter 40 to extract or pull fluid from the in vivo loop formed in the vasculature of the patient has a central venous pressure or cvp catheter 50 and an infusion or push catheter 60 concentrically and telescopingly mounted therein. As will be set forth below, each of catheters 40, 50 and 60 is positioned with a proximal end within a vessel in the patient's vasculature and a distal end in flow communication with the external unit U of the perfusion system P.

The catheters of the flow control unit 30 are located near the tumor to be treated. In the context of the present invention, near the tumor is intended to connote that the tumor is located in vasculature between the infusion catheter 60 and withdrawal catheter 40. Further, near the tumor is intended according to the present invention to signify that the catheters of the flow control unit 30 are located in the vasculature of the patient with no unoccluded intervening vasculature present in the area between the infusion catheter 60 and withdrawal catheter 40.

The larger or pull catheter 40 is a size, such as a 10 to 12 French or Fr. sheath 42, with a compliant distal balloon 43 or other comparable mechanism for occluding the vessel of interest in the patient. The pull catheter 40 also has a large enough internal diameter to accommodate the push catheter 60 and the central venous pressure catheter 50 concentrically and coaxially within it. Alternatively, the pull catheter 40 may, if desired, be sufficiently large, such as 14 Fr. sheath, that its distal end 41 may be used to occlude a vein without balloon 43.

The length of the sheath 42 of pull catheter 40 may vary based on the organ site and the venous access, for example neck or femoral cutdown. A sheath length of approximately 34 cm typically permits the catheter 40 be routed via a jugular cut-down procedure to the target organ site. The sheath 42 preferably is suitably flexible to permit extensive maneuvering and routing in the vasculature. However, the sheath 42 should also be structurally sturdy enough to avoid kinking or collapsing under pressure. The sheath 42 has a guide wire and/or introducer for proper placement. The guide wire or introducer is removed when the pull catheter 40 is established at the proper in vivo, closed loop position. An outflow port 46 (FIG. 4) on the pull catheter 40 is provided for the purpose of withdrawing fluids. A distal end 47 of the pull catheter 40 routes the outflow from pull catheter 40 to a withdrawal syringe 70 (FIG. 3) of the external unit U. A proximal end 48 of the pull catheter 40 is connected via a T-port 72 to the withdrawal or pull syringe 70 for withdrawing fluids.

The push or infusion catheter 60 has similar properties of length, flexibility and structural strength to those of the pull or withdrawal catheter 40. The push catheter 60 in the embodiment of FIG. 2A has a sheath 61 with an outer diameter of from about 3-7 Fr. fitted with a compliant balloon 62 for occluding a vessel. The sheath 61 is also provided with a radio-opaque proximal tip 64 for visualizing the position of the catheter proximal end within a vessel. The push catheter 60 has an outer diameter that enables it to fit coaxially and telescopically within the central venous pressure catheter 50 and the pull catheter 40. An opening 65 at the distal tip 64 of the input catheter 60 serves the purpose of infusing fluids. A proximal end 67 of the input or infusion catheter 60 is connected via a T-port 74 of the external unit U to a push syringe 76 for infusing fluids into the in vivo loop in the patient.

The central venous pressure or cvp catheter 50 has similar properties of length, flexibility and structural strength to those of each of the push catheter 60 and the pull catheter 40. In the embodiment shown in FIG. 2A, the central venous pressure catheter 50 has a sheath 51 with an outer diameter intermediate that of the push catheter 60 and the pull catheter 40. The central venous pressure catheter 50 is fitted at a distal end 52 with a port or opening 53 and in fluid communication with a pressure transducer 54. The pressure transducer 54 may, if desired, be located with the external unit U in fluid communication through the port 53 with pressure and flow rate conditions in the closed loop formed in the patient's vasculature by the present invention between the infusion catheter 60 and the pull catheter 40. The pressure transducer 54 allows monitoring of central venous pressure in the closed loop to be certain that a stable central venous pressure is present between the push catheter 60 and the pull catheter 40. A gauge or meter 55 or other form of pressure readout indication or display, as indicated schematically at 55, is present in the external unit U to indicate the central venous pressure sensed by transducer 54 to the monitoring/treating physician(s).

The pressure transducer 54 and indicator gauge or readout device 55 are connected to the central venous pressure catheter 50 for monitoring and tracking the central venous pressure in the patient's vasculature in the organ to receive perfusion between the push catheter 60 and pull catheter 40. The pressure transducer 54 and indicator gauge 55 thus provide the physician(s) with information about fluid conditions so that after formation of the closed loop at the treatment site, a steady state or frame of fluid pressure reference is obtained there. During the subsequent perfusion/treatment cycle, fluctuations or transient changes sensed through the transducer 54 and central venous pressure catheter 50 provide the physician with valuable information to closely control and monitor the infusion and extraction of fluid at the treatment site.

By virtue of the position of the three catheters relative to one another and to the target vessel, a pressure differential is established in the catheter network. One such pressure differential relationship is that of a transient stability established between the tip of the push catheter and the central venous pressure catheter. Another is the pressure differential between the push catheter and the background noise of the venous liver circulation. The pressure differential thus established is in a forward orientation and direction from the tip of the infusion catheter to the venous circulation.

In the opposite orientation and direction, a pressure differential is established between the pull catheter and the central venous pressure catheter. Another pressure differential is established between the venous circulation and the pull catheter. The perfusion treatment according to the present invention thus is in accordance with fluid dynamic and flow principles.

The push syringe 76 of the external unit U as connected via the T-port 74 to the push catheter 60 measures and injects the desired amount of various fluids during the treatment cycle, whether saline, dye, or therapeutic drug to be infused.

The external unit U also includes the withdrawal syringe 70 that is connected via the T-port 72 to the pull catheter 40 for collecting the spent fluid used during treatment, whether saline, dye, or drug, once the fluid has been infused and passed through the closed loop treatment site. Each of the syringes 70 and 76 is further connected to its respective associated pump 71 and 75, such as a Harvard type infusion pump, for the purpose of infusing and withdrawing the saline, dye, or drug, as the case may be. The infusion by syringe 76 and withdrawal by syringe 70 is done by the physician with the external unit U at the desired flow rate, and also to set up the differential pressure and related motions to physically impart characteristics to the fluids at the perfusion treatment site.

According to the present invention, the external unit U includes a computer C which obtains, organizes, stores and present data and images to a treating physician or physicians during the retrograde perfusion procedure. The data and images are available from the computer C on a real time basis and include, for example, data relating to the operation and functioning of the internal flow control unit F. The data include data from or relating to operation of the multicatheter flow control unit 30 such as infusion rate, withdrawal rate, fluid displacement, pressure concentration and other fluid flow and pressure parameters and measurements.

The operation of the syringes 70 and 76 and their respective associated pumps are preferably automated via the computer C and associated computer control instructions, or software. As will be described the computer C and associated software instructions allow for the monitoring, organization, presentation and storage to treating physicians of multiple measurements, data and records relating to the patient and the retrograde perfusion treatment on a real time basis of multiple disparate measurements and item of data as the retrograde perfusion procedure is in progress. The computer C and its associated software operate in the fluid monitoring phase according to established settings, taking into account various factors, such as:

(1) the volume of fluid (saline, dye, drug) to be infused;
(2) the rate of infusion of the fluid(s);
(3) the time duration of the infusion; and
(4) the ratio of withdrawal rate to infusion rate.

In addition, the computer C and software permit a database to be formed and maintained. The database so formed may be maintained and updated in the computer C and may also be networked and made available on a real time basis via data communications links such as wire, optic, radio wave, satellite or other communications media to other computers and data storage systems and facilities. The database contents of the computer C and other computer systems in communication therewith also preferably includes data relating to the patient's history and present condition, current heart rate, blood pressure, respiration and temperature obtained in any suitable conventional manner, as well as data records from prior treatments or surgeries.

The computer C also is in communication with the visual monitor M and the imaging mechanisms, such as a scanner S, fluoroscopy and the like. The computer C receives data the content of the content of the image from such imaging mechanisms and includes such data as image data in the database. The image data is available for 3-D high resolution imaging to observe or define spatial boundaries or borders, or densities of portions of the body under treatment or investigation. The image data and the physiological monitoring data also allow monitoring and observation of the response to therapy at the cellular level. The database allows data to be retained in order to correlate the location of various perfusion treatment sites, and established settings, as well as the factors mentioned above, along with the type and nature of images or fractals obtained therewith. Such a database allows, as will be set forth, a physician greater flexibility in treatment by retrograde perfusion.

The computer system of the computer C and its associated computer executable instructions or software described herein is capable of organizing disparate sets of data in the form of signals or other information media from various sources, organizing the data, time-stamping the data, and presenting the data for use by a physician in the course of a treatment procedure.

The computer C (FIGS. 3 and 4) includes a processor or CPU 80 which operates under the control of a series of computer-executable instructions. The instructions may be contained in memory 82 of the computer C, or on magnetic tape, conventional hard disk drive, electronic read-only memory, optical storage device, or other appropriate data storage device. Also, the instruction may be stored on a data storage device with a computer readable medium, such as a computer diskette, having a computer usable medium stored thereon. The CPU 80 is connected by input/output interfaces 84 to components of the perfusion system for data transfer purposes. The CPU 80 receives data from the catheters 70 and 76 and other components of the external unit U, as well as the monitors M and imaging mechanisms described above. The CPU 80 also includes a data display screen 86 for the computer operator, as well. The CPU 80 is also networked, as described above, with other computer systems for database compilation, transfer and storage purposes. Generally, at least one computer includes a file serve capability for database retention and master storage purposes. Also, if desired, the computer networked computer C may include a mainframe computer of any conventional type of suitable processing capacity. Other digital processors, however, may be used, such as a laptop computer, or any suitable processing apparatus at any of the computer sites in the network.

A flow chart T (FIGS. 9-13 herein) illustrates the structure of the logic of the present invention as embodied in computer program software. Those skilled in the art will appreciate that the flow charts illustrate the structures of computer program code elements that function according to this invention. Manifestly, the invention is practiced in its essential embodiment by a machine component that renders the program code elements in a form that instructs a digital processing apparatus (that is, a computer) to perform a sequence of function steps corresponding to those shown.

It is important to note that, while the present invention has been, and will continue to be, described in the context of a fully functional computer system, those skilled in the art will appreciate that the present invention is capable of being distributed as a program product in a variety of forms, and that the present invention applies equally regardless of the particular type of signal-bearing media utilized to actually carry out the distribution. Examples of signal-bearing media include: recordable-type media, such as floppy disks, hard disk drives, and CD ROMs, and transmission-type media such as digital and analog communication links.

With reference to FIGS. 9-13, there is depicted a high-level logic flowchart illustrating a method according to the present invention. The method of the present invention performed in the computer C can be implemented utilizing the computer program steps of FIGS. 9-13 stored in memory 82 and executable by system processor 80 of computer C and the data resulting from the data collection steps performed by the components of the perfusion system F connected to the computer C, as described above.

Several classes of data sets are to be controlled and synchronized by the computer system C of the present invention. There are
1) catheter control and monitoring data,
2) 3-D graphic modeling of data captured from fluoroscopy or other imaging techniques,
3) patient history data,
4) physiological monitoring data, and
5) predictive statement.

The flow chart T illustrates computerized monitoring according to the present invention of a retrograde perfusion treatment procedure. The system and means described herein is capable of organizing disparate sets of data in the form of signals or other means from various sources, organizing the data, time-stamping the data, and presenting the data for use by a physician in the course of a treatment procedure.

The flow chart T (FIGS. 9-13) illustrates the flow and interchange of information from the computer C from start to end of a retrograde perfusion treatment procedure. The preliminary steps (FIG. 9) include system initialization and system readiness. In the first stage also illustrated in FIG. 9 patient data is input and verified. The patient data sets include demographic patient data, patient history data, and current patient physiological monitoring data.

In the second stage of the flow chart T (FIG. 10), the computer system C operates to aid in visually guiding the proper placement of each catheter, in properly inflating each balloon, and in initiating the saline infusion to achieve the desired stability of the catheter system.

In the third state (FIG. 11), the system C initiates the catheter start-up subroutine with the infusion of radioopaque dye to aid in monitoring the catheter system flow dynamics including the hydrostatic, hydrodynamic, hydrokinetic, and hydrokinematic attributes.

In the fourth stage (FIG. 12) delivery routes are confirmed as data from the fluoroscopic image is video captured and modeled in high-resolution 3-D graphics. The physician may query and examine data from both the local and the central database to obtain a predictive statement and to select a delivery route and treatment process.

In the fifth and final stage (FIG. 13) the physician has verified the delivery routes and begins the administration of a therapeutic agent. Each cycle of delivery of therapeutic agents during the treatment process is completed when the agent has traversed the route from input to withdrawal.

Figure 13:
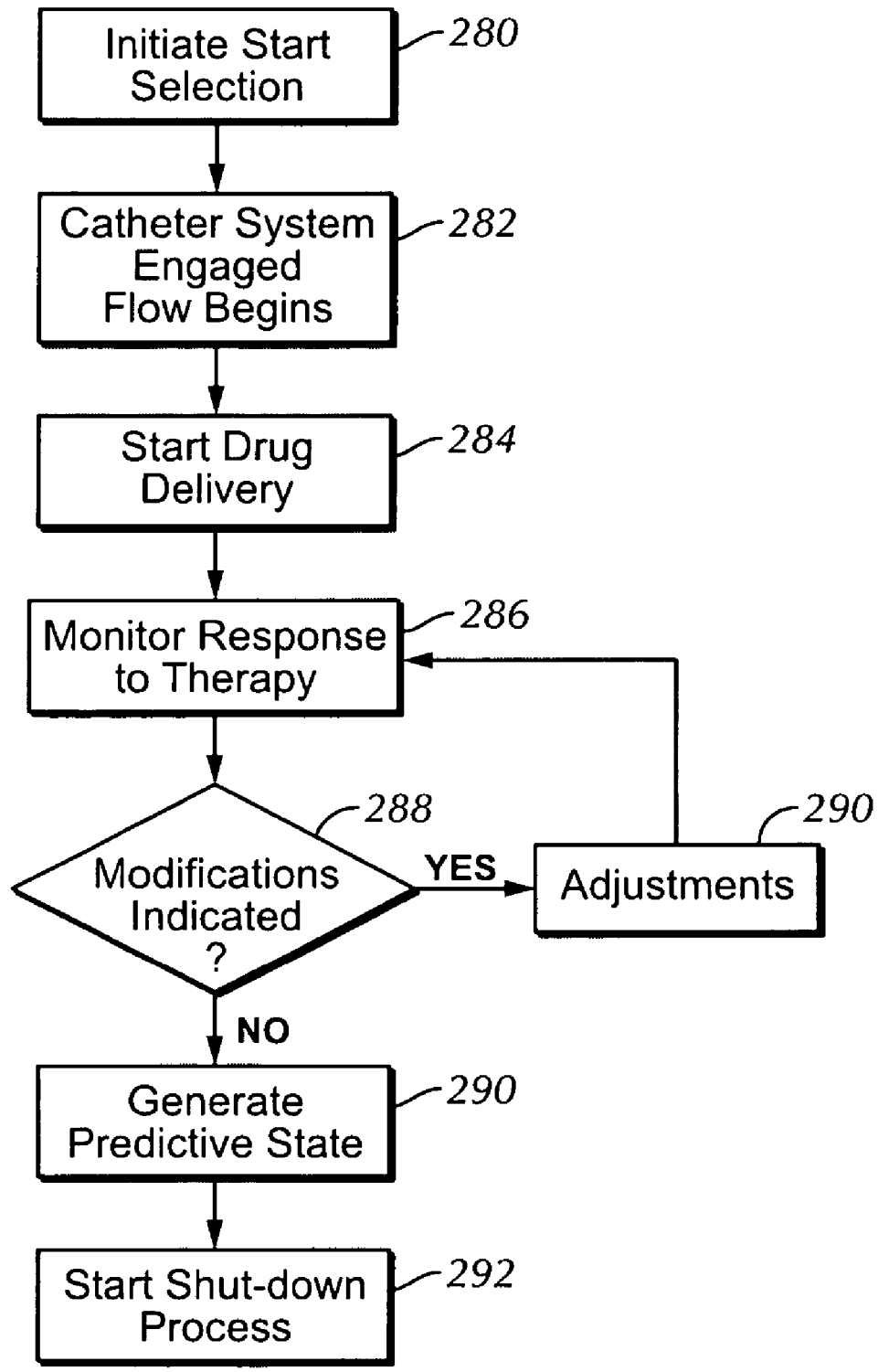

During the treatment process, as shown in FIG. 13, the computer C under control of the operating instructions monitors the patient's condition, including response to therapy. Prior to shutting down at the completion of the treatment process, predictive and suggested action states for future treatment to the patient are presented to the physician, then the system shut-down process occurs.

To initiate a treatment procedure, the system is appropriately initialized. An initial step 200 (FIG. 9) includes system initialization and system readiness procedures of the conventional type. As indicated, if the system initialization step is determined to be not properly completed, a re-boot step 201 is performed. The process continues until satisfactory initialization occurs.

Next, following system initialization a step 202 existing patient data is input into the computer C from the database and verified. The patient data sets include demographic patient data, patient history data, and current patient physiological monitoring data. A query input is entered simultaneously as indicated a steps 204a and 204b at the local database and the remote central repository, respectively. Data in each of the local and remote databases is polled to determine proper patient scheduling.

If a patient is not scheduled in either of the local or remote databases, the computer displays a "not ready" alert. If the patient is properly scheduled, the computer displays a "system ready" alert, as indicated at 206.

When the system is ready, a series of prompts request the user to input the set of patient identification data. A patient identifier code, number or other indicator is prompted to be entered at step 208. The computer system performs a search of the archived patient history data library to determine if the patient is a new or established patient. If the patient is a new patient, a prompt step 210 requests the user as indicated in step 211 to enter the set of patient history data and the data is archived in the central repository.

If the system finds the patient to be an established patient, the system performs a data mining function as indicated at step 212 to yield data regarding the patient's prior history and, as indicated at step 214, presents the results to the physician. In addition, given the patient's history, the computer system during step 214 makes predictions as to what treatment options might be best suited to the patient's current situation and presents its predictions to the physician.

Figure 9:
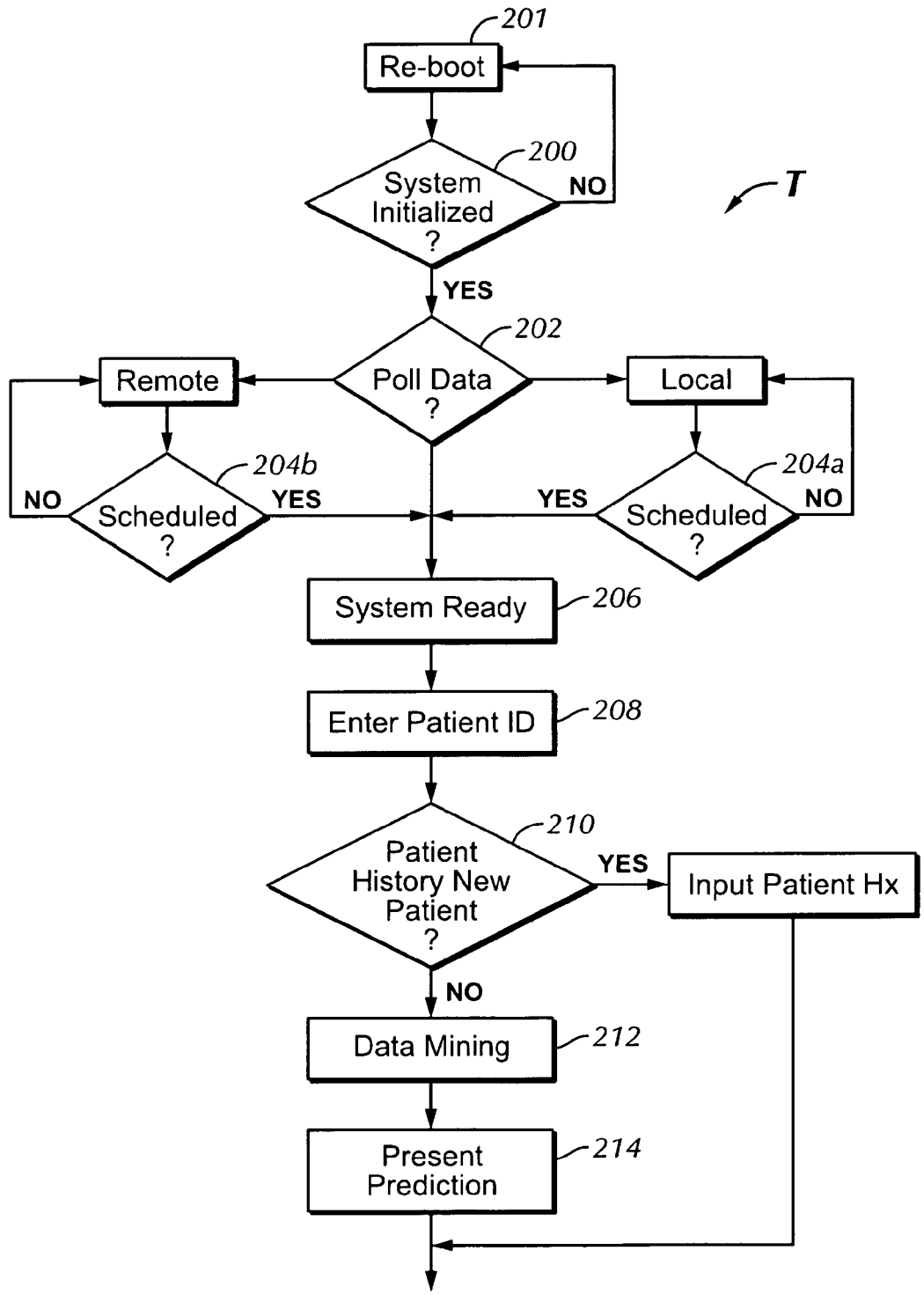
FIGS. 9, 10, 11 12 and 13 are functional block diagrams of computer processing steps according to the present invention.
Figure 10:
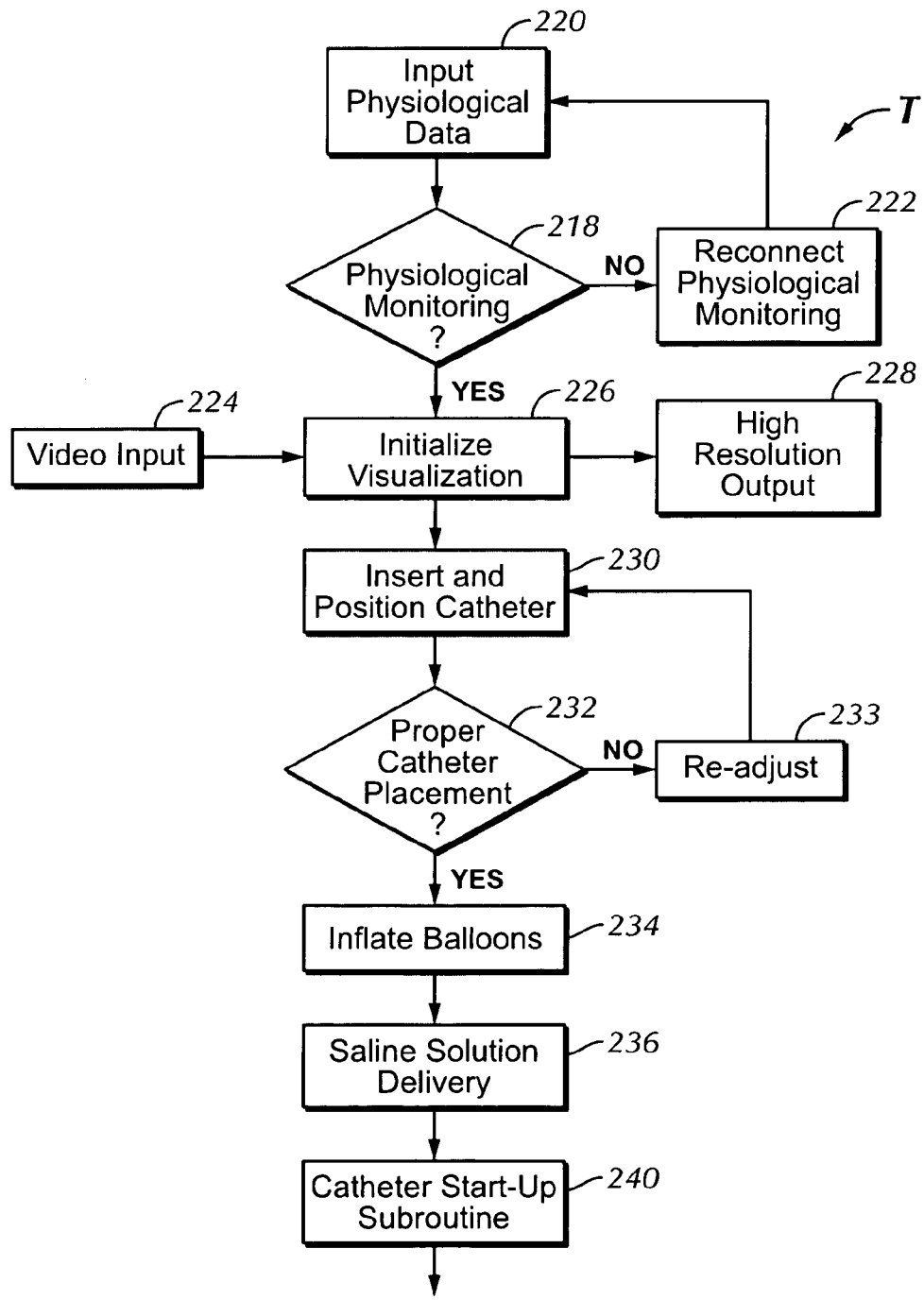
Figure 11:
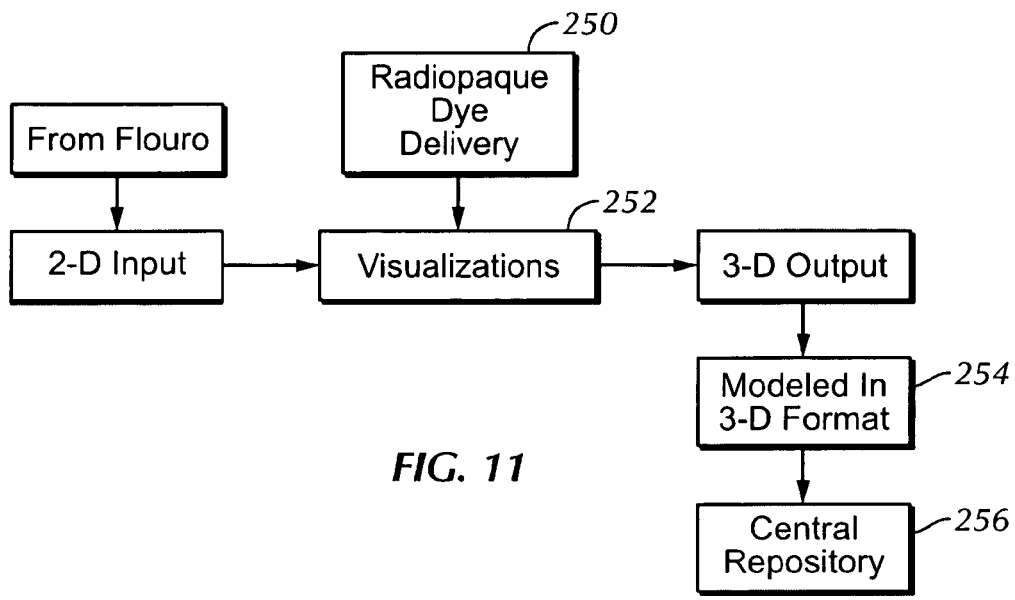
Figure 12:
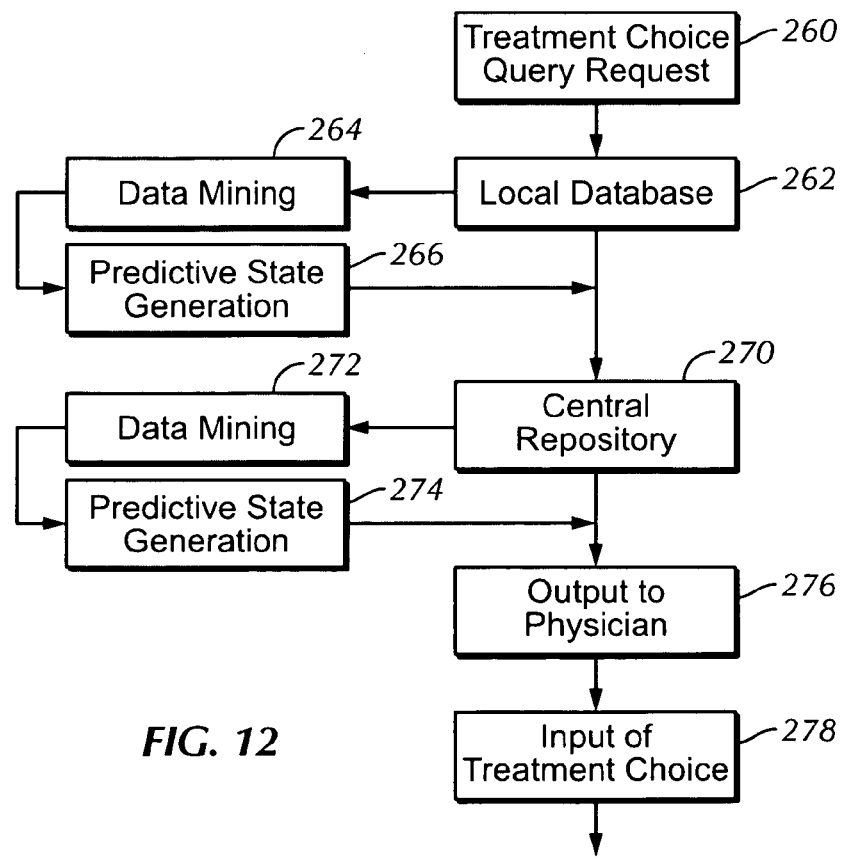

After the patient demographic and historical data are entered, analyzed and archived, as under control of the steps illustrated in FIG. 9, a physiological monitoring sequence illustrated beginning at step 218 in FIG. 10 is next performed. When patient history data is archived during procedures in connection with the present invention, physiological data are obtained include, for example, heart rate, blood pressure, temperature, pulse, respiration, $CO_2$ and the like, and are input as indicated in step 220 into the database from various transducers and monitors. The different types of such physiological data are archived, continuously updated and presented on the workstation monitor, such as 86 (FIG. 4) throughout the subsequent treatment procedure, as indicated in FIG. 10. The computer system C thus continuously monitors all physiological data and alerts the physician of any deviations from the normal physiologic parameters. If a transducer is detected as not being connected, prompts or signals may be sent out during a step 221 to inform the treating physician and staff that reconnection needs to be made for physiological monitoring by that transducer.

Steps 224, 226 and 228 in the flow chart T shown in FIG. 10 subsequent to step 220 cause the computer system C to receive a video input, permit initial visualization of the treatment area and form a high resolution output image. These steps aid the physician in visually guiding the subsequent proper placement of each catheter, properly inflating each balloon, and initiating a hydrostatic phase, and infusing a saline infusion to achieve the desired stability of the catheter system of the flow control unit F.

The initial phase of catheter placement is that of assembly of the flow control unit F based on the planned perfusion treatment, the treatment site and other factors. Assembly can be regarded as a sequential assembly phase. The catheters 40, 50 and 60 are combined externally in sequence and placed sequentially coaxially relative to one another. In one possible configuration of the catheters shown in FIG. 2A, the pull or proximal catheter 40 is the outermost catheter of the three. Coaxially positioned within the pull catheter 40 are the catheters 50 and 60, which are sequentially placed based on their respective sizes. In the embodiment of FIG. 2A, the next catheter to be positioned coaxially within the pull catheter 40 is the central venous pressure or cvp catheter 50. Coaxially positioned within the central venous pressure catheter 50 is the innermost chamber and catheter, the push or distal catheter 60.

Figure 2B:
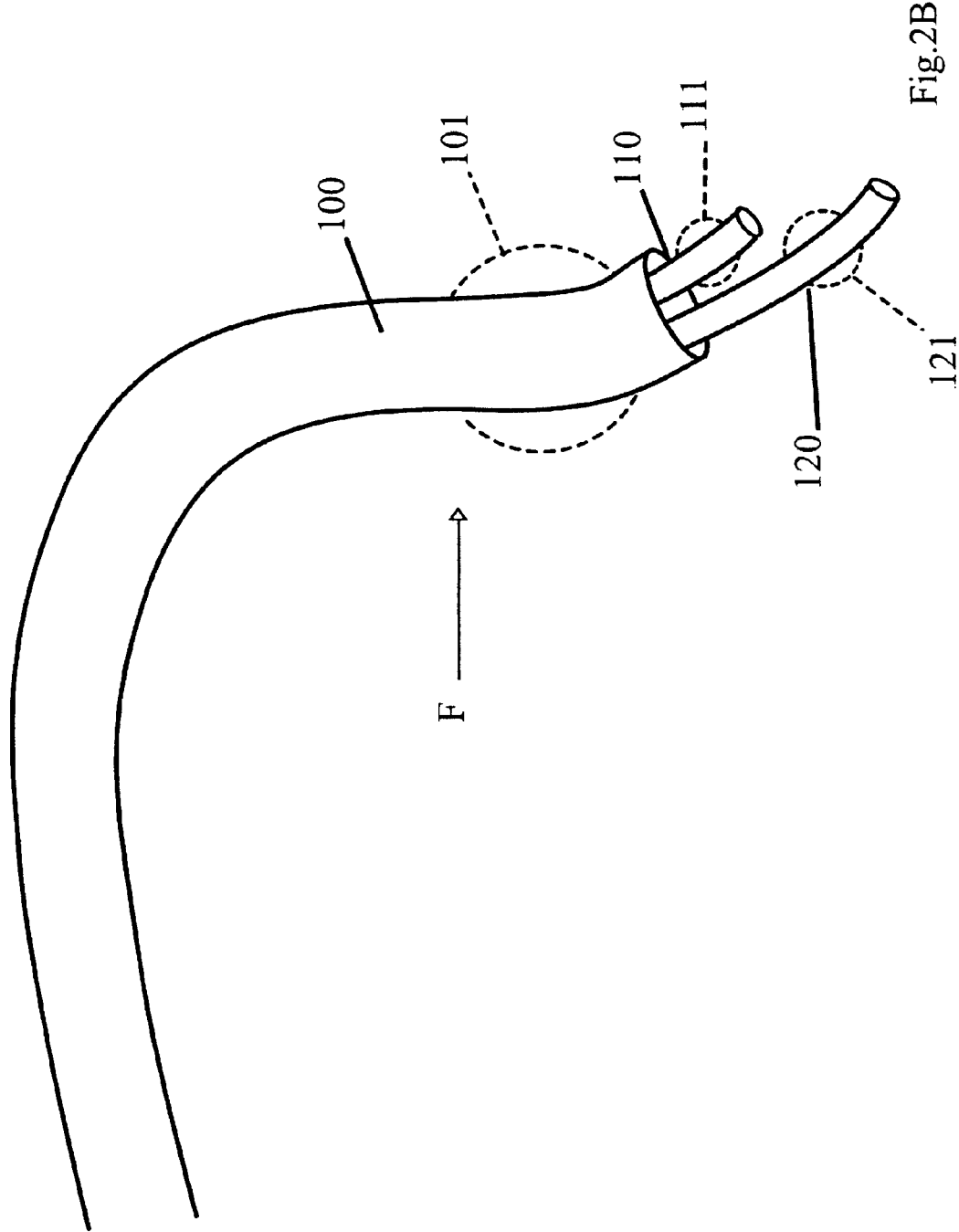

Assembled telescopically one inside the other in this manner, the three catheters 40, 50 and 60 form the internal flow control unit F. As noted above, it may in certain instances be desirable for the catheters 40, 50 and 60 to have an alternate configuration. For example, as shown in FIG. 2B, an outer catheter 100 with balloon 101 serves as the pull catheter, and catheters 110 and 120 with their respective balloons 111 and 121 are separately and not co axially mounted with each other serve as the central venous pressure catheter and the infusion or push catheter, respectively. Appropriate connections to the respective syringes and pumps of the external unit U are made for these purposes.

Alternatively, the outer catheter 100 shown in FIG. 2B may serve as the central venous pressure catheter and the catheter 110 serve as the pull catheter, if desired. Again, appropriate connections to the external unit U are made for this purpose.

The control unit F with catheters of the various configurations identified above allows the physician to develop various strategies for how to organize differential pressures externally between the push syringe 76 and the pull syringe 70 for moving fluid outward through the perfusion system P to the closed loop to the treatment site and returning. The fluid movement is accomplished under control of the computer system C using the pressure-monitoring central venous pressure catheter 50 to coordinate, monitor, and visualize transient changes in central venous pressure sensed through catheter 50 during the operation of the internal control unit F.

The assembly of the control unit F and the final determination of its configuration is adjustable with regard to the relative longitudinal placement of the catheters 40, 50 and 60 with respect to each other. Further, the configuration and location of the catheters 40, 50 and 60; the infusion flow rate and pressure; and the extraction flow rate and pressure may be monitored and adjusted "on the fly" with the computer system C under control of the treating physician while the retrograde perfusion is under way. The adjustments may be based on the variable requirements of the target vessel (i.e. vessel diameter, length) as well as on the objectives of the planned, controlled treatment that is to be performed to frame a search for a missing piece while trying to frame a strategic action and a strategic course of retrograde perfusion treatment, including apriori goals of a visual representation of mapping of a volumetric shape based upon an emergent shape.

Prior to catheter placement and prior to beginning the hydrostatic phase, catheter attributes for the catheter of the flow control unit F (FIG. 2A or 2B) being used are also input to the database of the computer system. Catheter specifications, connectors, connector sites, and balloon specifications for each catheter are input manually into the database and archived in the central repository. Catheter balloon specifications are also input to the database and archived. In addition, the input and withdrawal syringes 76 and 70 are filled with a desired volume of saline solution and the automatic pumps are set at the desired flow rate. This information also is archived in the central database.

Each catheter of the flow control unit F is fitted at both ends of each lumen with a transducer, and as needed, the transducers measure proprietary attribute data at each of the external and internal ends of each lumen. Data from the transducers are archived in the central repository and made available to the physician during the procedure. To achieve proper catheter placement, the physician manually guides each of the three catheters respectively to the target vessel, as indicated at step 230. As indicated at step 232 and 234, catheter position is observed and re-adjustment of catheter position is made by the physician until satisfactory placement is achieved.

A visual representation (FIG. 8) of the type shown on video monitor M illustrates the successful placement of the catheters 40, 50 and 60 in order within a target vessel, in this case an animal liver L. The pull catheter 40 is inserted first in sequence into the external jugular vein and routed with the help of guide wire 45 into the desired location of the venous vasculature of the liver selectively toward the target area. Subsequently in time the stable central venous pressure catheter 50 is threaded coaxially within the pull catheter 40 to its desired location distal to the tip of the pull catheter 40. Then, the push catheter 60 is threaded coaxially within the stable central venous pressure catheter 50 and is pushed forward via a selective route to a destination point within the target organ L. At the destination point, the catheters 40 and 60 are seated at their respective desired occluded positions in the vasculature. The sequential assembly of the flow control unit F is thus completed.

In the foregoing initial stage, the three catheters 40, 50 and 60 are put in position in a selected venous site with no flow through the control unit F. With the catheters in place and without initiating flow, the measurement of the central venous pressure by transducer 54 gives a real-time initial model of the system fluid dynamics of blood at the treatment site.

As the manual placement process is visualized on fluoroscopy, the image of the catheters is captured and input to a computer graphics system of the computer C which renders the image on the workstation monitor 86 to aid the physician in proper placement. Having confirmed the proper catheter configuration and placement, the balloons are at step 234 inflated as needed to occlude the vessel, to insure a tight seal, and to prevent collateral leakage.

Then, to insure that a state of hydrostatic equilibrium exists between each of the push, pull, and central venous catheters and the organ, the external central venous pressure is measured and recorded in the database.

At this point the catheter configuration is considered fixed and the position of each catheter is input into the database as a topographical coordinate. Then the time is set to zero at the pump connected to each of the push and pull syringes and at each end of the external and internal catheter lumens.

As the saline solution delivery procedure begins during step 236, the motion of the pull syringe produces a vacuum that guides the saline from the tip of the push catheter toward the pull catheter. As the flow of saline travels from the tip of the push catheter and into the countervailing force of the hepatic flow, a resonant pattern results. This resonance is monitored and registered in the database.

Because the infusion of saline is not visible on fluoroscopy, the computer system C monitors the fluid cycle and registers the completion of distinct fluid trajectories. The completion of one fluid trajectory is registered as the saline flows from the tip of the push syringe to the tip of the pull syringe. Another and simultaneous trajectory is registered as the saline flows from the external tip of the push catheter 60 to the external tip of the pull catheter 50. A third and simultaneous trajectory is registered as the saline flows from the internal tip of the push catheter to the internal tip of the pull catheter. The different trajectories of the hydrodynamic phase are monitored independently yet simultaneously by the system and the data is input into the central repository.

As the hydrostatic phase ends, the catheters are in position, the fluid forces are in equilibrium, and the spatio-temporal coordinates are registered; the data relating thereto is input into the central repository. The computer system C temporally synchronizes all the data and the system is ready to begin stage 3, the catheter system start-up routine of step 240 (FIG. 10) which marks the beginning of the hydrodynamic phase.

At the start of the hydrodynamic phase it is important to distinguish the various parallel, dynamic data sets that must be monitored, synchronized, and integrated. A first distinction is made between external parameters and internal parameters. A second distinction is made between push flow parameters, pull flow parameters, and central venous pressure parameters. A third distinction is made between input trajectories and withdrawal trajectories.

The first set of attribute data is the external parameters. One set of external parameters is the volume of saline to be infused, the infusion rate in ml/min, the orientation of flow, and the withdrawal rate in ml/min. These quantities are input into the database and, because infusion and withdrawal are to occur simultaneously, the system marks the start time at zero for each of the input and withdrawal syringes 76 and 70, respectively.

A second set of attribute data is the internal parameters. The internal parameters are the infusion rate in ml/min through the push catheter, the flow pressure, the withdrawal rate in mi/mm through the withdrawal catheter, and the central venous pressure. The system marks the start time at zero for each of input and withdrawal catheters. The rate of infusion through the push catheter, the rate of withdrawal through the withdrawal catheter, and the central venous pressure are monitored continuously as signals and are input into the database for synchronization.

Having completed the hydrodynamic stage of saline infusion, the physician begins the hydrokinetic phase of radiopaque dye infusion through the established route created previously by the saline. Attribute data for this phase include the volume of radiopaque dye, its density, its concentration, the rate of infusion, and the rate of withdrawal. The time is set at zero, the data is input into the central repository and the dye infusion begins. The computer C system during step 240 initiates the catheter start-up subroutine with the infusion of radio opaque dye to aid in monitoring the catheter system flow dynamics including the hydrostatic, hydrodynamic, hydrokinetic, and hydrokinematic attributes.

Next, (FIG. 11) a radio-opaque dye delivery step 250 occurs, during which a radio-opaque dye is added into the saline solution already present in the closed loop flow path established as described above. The dye-containing solution is allowed to flow into the perfusion site so that a CAT image may be formed on monitor M of the catheter placement site. With the infusion of the radio-opaque dye and the resultant image formed on the monitor M, a visible, physically-imparted characteristic pattern emerges in real time of the region within the organ between the distal ends of the push or infusion catheter 60 and the pull catheter 50. The image is also formed at the same time that the treatment administering catheters are in vivo at the site where retrograde perfusion of the organ is indicated. The image so formed provides a visible indication on the display monitor M of the established flow path. Thus, during step 252 shown in FIG. 11, delivery routes are confirmed as data from the fluoroscopic image is video captured and modeled in high-resolution 3-D graphics during step 254 for display on the monitors M. The 3-D graphic data so obtained are stored in the central repository during step 256.

As the radio-opaque dye fills the topographical region previously demarcated by the saline injection, the resonant pattern of flow known as a fractal appears as a 2-D image on the fluoroscopy screen. Attribute data from the 2-D fluoroscopy image is video captured, time stamped, and input into the computer graphics system of the computer C. The system correlates the flow data with 2-D fluoroscopic fractal image and renders the image as a high-resolution 3-D interactive model during step 254.

The high resolution model and corresponding flow parameters are archived in the central repository during step 256 and presented on the workstation display 86 as time-stamped flow data in 3-D, enabling the treating physician to interact with and manipulate the dynamic image.

At this point the computer system C as indicated at step 260 (FIG. 12) offers a query option to the physician. Given the system's extensive knowledge base regarding up-to-the-minute treatment modalities, pharmacokinetics, and the patient's condition, the computer system C has the capability of data mining to find the optimum therapeutic course to take for the current situation.

The physician may as indicated at step 262 query the local database to ask what drug would be the most effective, in the given situation, what dose rate to use, for what duration, etc. The computer system C software performs a data mining function as indicated at step 264 and predictive state generation function as indicated at state 266 or the contents of the local database and presents the treating physician a suggested course of action on the display 86.

Also at step 270, the physician may similarly query the central repository for the same information. The central repository again perform similar data mining and predictive state generation functions as indicated at steps 272 and 274 of the contents of the central database and presents the results to the treating physician.

Optionally, physicians as indicated at steps 276 and 278 may choose to use their own knowledge base and experience along with their own familiarity with the patient to determine the proper course of action and provide this information as inputs to the computer system C for inclusion in the knowledge base stored therein. The ultimate decision in regard to the course of action is in the hands of the physician.

Also, because the computer system C can track the flow dynamics at a microscopic level beyond human perception, physicians can query the local database, query the central repository, or trust their own experience in determining the need for adjustments to the catheter system to validate system stability and to insure that no systemic leakage occurs prior to the infusion of therapy.

Once the required confirmatory data is registered in the central repository, the computer system C makes a comparative analysis with previous procedures and presents the physician with a predictive state or suggested action states.

With the continuous 3-D modeling and the continually updated flow parameters available on the workstation monitor in real-time, the physician prepares to initiate the treatment procedure and as indicated at step 280 makes appropriate entries regarding attribute data into the database(s) of the treatment choice.

Attribute data for the treatment phase includes the name of the drug or drugs, and for each drug the volume, the flow rate, the concentration, the order of infusion and the threshold, intensity and duration of flow or time-on-target.

The present invention thus allows direct control and definition or establishment of the retrograde perfusion flow path for delivery of therapy by retrograde perfusion to an organ site in the body. The image so formed also serves to allow the treating physician to formulate, predict and establish probable routes and trajectories to be taken thereafter by a desired therapeutic agent. As can be seen, a definite and definable flow path, and in effect an in vivo flow map of the perfusion site, is formed and depicted. The treating physician is not presented with a vague and undefined image of the organ and flow path of the therapeutic agent.

As a result and as indicated in the steps illustrated in FIG. 13, the physician has verified the delivery routes during step 282 and thereafter at step 284 begins the administration of a therapeutic agent. The chemotherapeutic agent is introduced at the established treatment site. The physician can with the in vivo loop so formed develop various strategies for the flow control unit F. The physician is given alternatives by using the flow control unit F as to how to organize differential pressures externally between the push syringe 76 moving fluid forward and the pull syringe 70 moving fluid outward through the in vivo loop formed at the tumor treatment site.

If desired, different chemotherapeutic agents, different dosages, different sequences and exposure times and various combinations of any one or more of these chemotherapeutic strategies may be implemented with the present invention while the flow control unit is at the treatment site. The pressure-monitoring central venous pressure catheter 50 is used to coordinate, monitor, and visualize transient changes in the central venous pressure at the in vivo treatment site during the operation of the flow control unit F. As noted, the closed loop in vivo flow path has been established and verified before the administration of the chemotherapeutic agent.

The chemotherapeutic agent may, in addition to doxorubicin previously mentioned, be any of a number of treatment agents. Other treatment agents which are effective as anti-cancer treatment agents may, for example, include cyclophosphamides such as those known as Cytoxan®, and others; methotrexate; and prednisone. The present invention, with its closed loop flow path and mounting pressure within such a flow path is particularly adapted for administration of chemotherapeutic agents having possible side effects on other organs, even potentially severe side effects. An example, as mentioned above, is doxorubicin. The delivery process is completed when the agent has traversed the route from input to withdrawal.

When the push syringe has been filled and the time has been set at zero, the delivery of therapy begins at step 284, as indicated previously. As the drug cycles through the predetermined route, the therapy is monitored as indicated at step 286. Physiological measurements are updated and cellular response is measured. During treatment, as indicated at step 288, modifications in the treatment may be indicated. These may result from observations of the patient's physiological data, the location of the catheters, images of the treatment in progress, comparisons of current data with data stored in one or more of the databases, or some combination of these, or other factors. As indicated at step 290, adjustments may be made as required and monitor continued during step 286.

The data obtained during step 286 is input into the database and presented on the workstation monitor 86 for the physician to use for right-time, on-line decision-making. When the desired end state is achieved, the infusion of drug is halted, and saline is washed through the catheter system. All end state parameters are registered and input into the central repository.

Throughout the treatment process, the computer system C is tracking the patient's physiological condition. In addition, computer system C registers reaction to therapy at the cellular level and monitors the ongoing response.

Prior to finalizing the procedure, given its knowledge base regarding the patient's history and present condition, the computer system C performs a comparative data analysis and as indicated at step 290 generates a predictive state and suggested action state as to what future treatment options might be best for the patient. This information is presented to the physician to aid in future decisions and courses of action for the patient.

In the final stage during step 292, the catheters are withdrawn, all data is time stamped, updated and archived, and the system is shut down.

Figure 8:
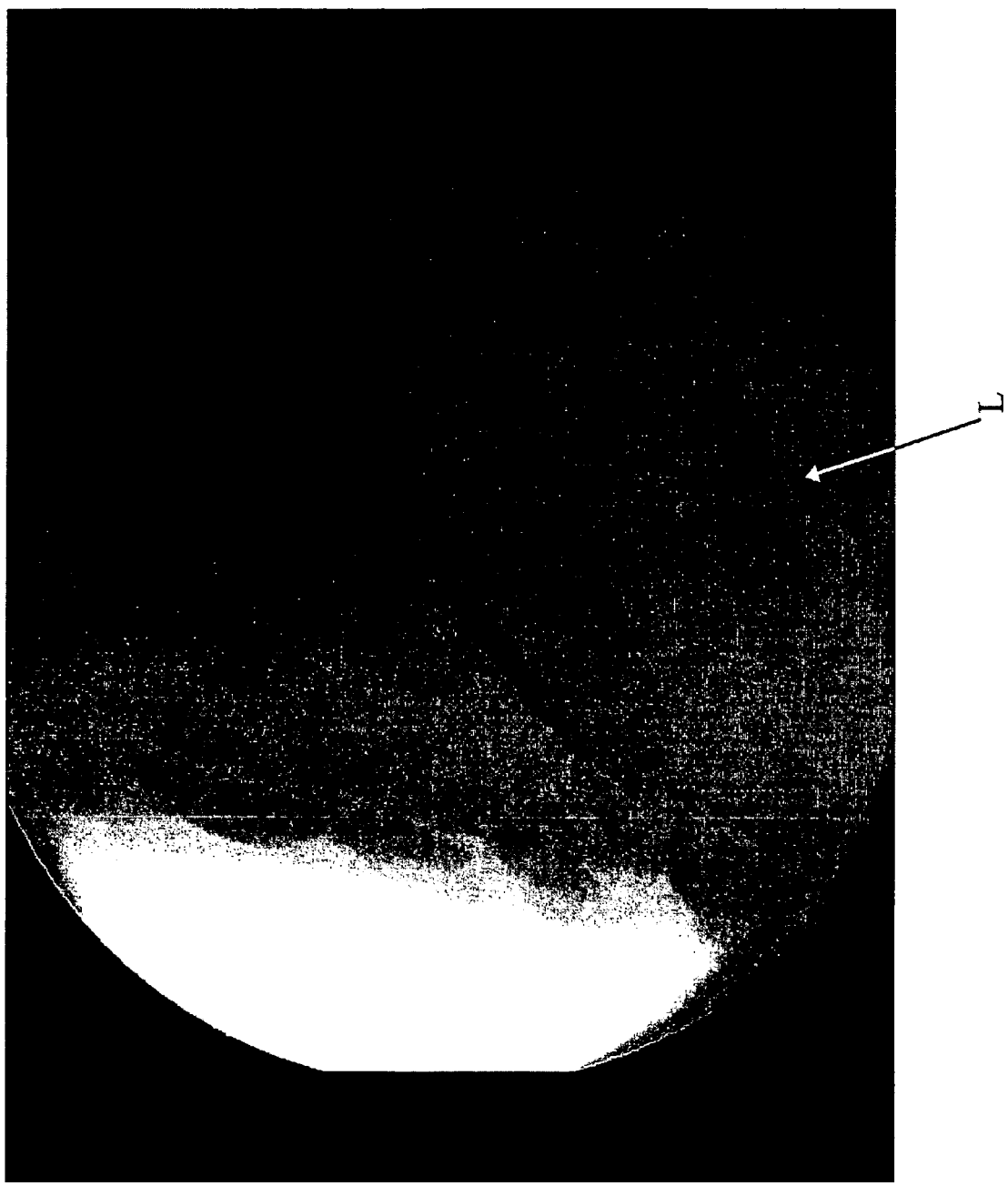
FIG. 8 is a display image of an animal liver during a perfusion treatment procedure according to the present invention.

FIG. 8 is, as noted above, a photographic image of such a flow path established in this manner. The image so formed can be considered as an in vivo volumetric fractal map of the fluid trajectories induced in the organ under treatment with the present invention. The map or image so formed serves as a visible record, much like a fractal map, of each of the three-dimensional volume, two-dimensional area, and perimeter of the controlled dynamic flow routes taken by infusates from the proximal end of the catheters to the outer boundary of the organ for an during retrograde perfusion. Several advantages result from such volumetric mapping. Current techniques of visualization provide no means to analyze self-similar fractal anatomical structures from the inside and extending to the outer boundary of the vascular venous tree. Nor do current techniques enable the correlation of the geometrical-visualizable properties of a physiological system with its dynamic physical properties. The image so formed also serves to allow the treating physician to formulate, predict and establish probable routes and trajectories to be taken thereafter by a desired therapeutic agent.

The system thus described can be said to have both fixed and variable properties. The fixed properties refer to the fixed position of each of the three catheters. The variable properties refer both to the background noise dynamics of the hepatic circulation, i.e. the hepatic artery, the portal vein, and the hepatic veins, and to the variable hydrodynamics of the fluid trajectories and wave motions induced by the actions of the push, pull and central catheters. The fixed and the variable aspects of the system are coupled together, and inextricably interrelated.

There is, however, no need to establish or define specific fluid flow equations of motion explicitly in order to verify that proper perfusion fluid flow paths and relations are established. The control or treatment unit functions as an analog fluid dynamic computing unit that during its use and operation implicitly computes the solution to the equations of motion for the network, and performs the perfusion treatment according to the desired flow paths and relationships. This is done without resorting to the explicit use of calculations, numbers, mathematical equations or physical equations of motion and such; the control unit during its use performs those kinds of computational tasks.

Two examples or models help to explain by analogy the kinds of differential equations of motion that are implicitly solved by operation of the control unit. One is a water-flow model that cascades; the other is a moving crowd model.

In the water-flow model, the size and shape of the catheters influence the motion of fluid through the catheters. Also, the motion of fluid in parallel and opposite directions, and orientation through the catheters and through the vascular beds obeys the physical laws related to pressure, flow rate, and volume. In the moving crowd model, the size and shape of the catheters influence the movement of particles through the catheters. Also, the movement of particles through the network conforms to the physical laws related to pressure, flow rate, and volume.

As shown in FIG. 8 an iodinated contrast material has been injected with the control unit F into a peripheral branch of a hepatic vein of an adult laboratory animal. FIG. 8 was obtained with the retrograde perfusion procedure described above in an equilibrium phase and with a net pressure of from about 8 to about 10 mm Hg. It is to be noted that opacification is obtained of the branches, with minimal parenchymal stain. Further, no opacification of the adjacent hepatic or portal veins is seen present.

Figure 7:
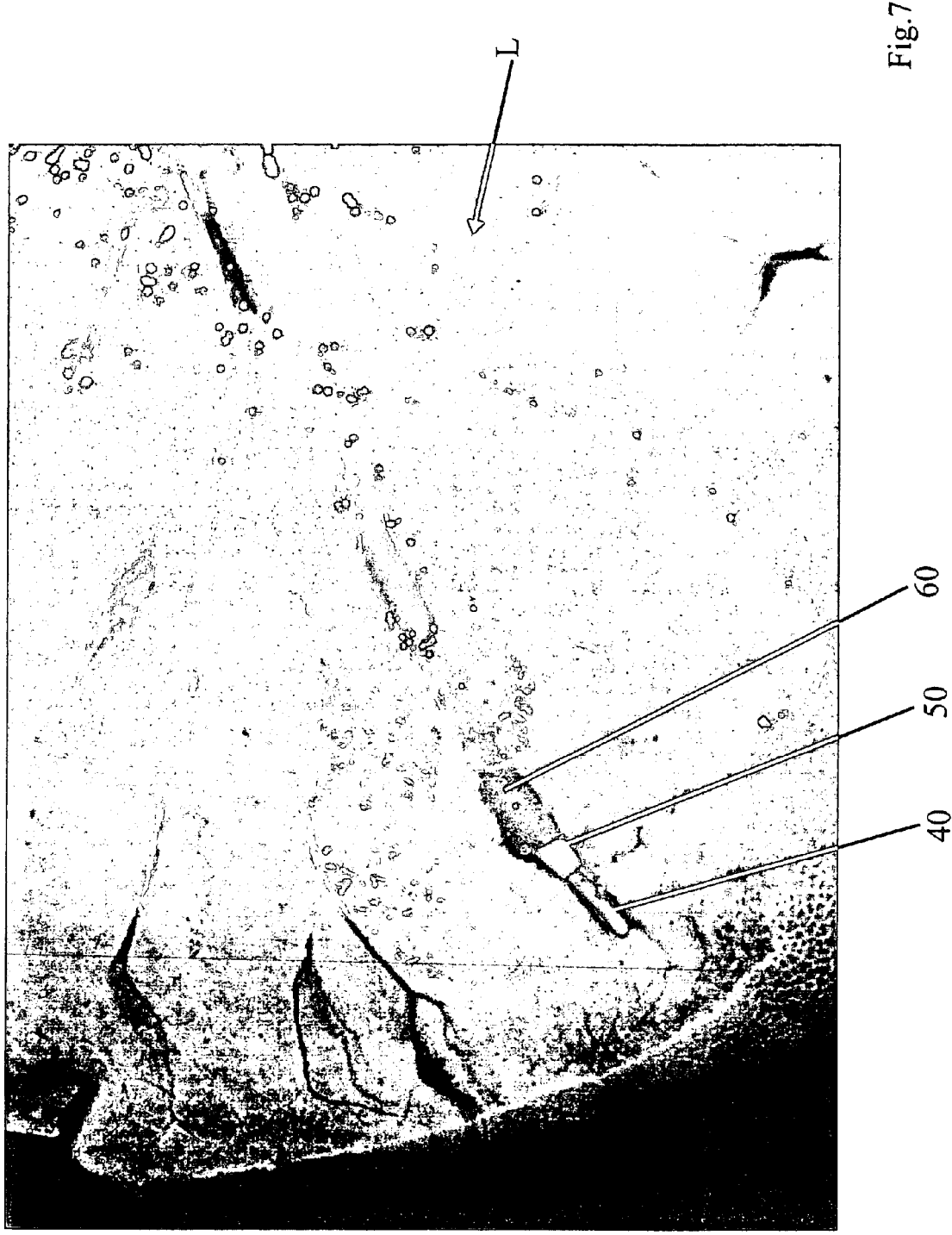
FIG. 7 is a photograph of an animal liver after a perfusion treatment procedure according to the present invention.

FIG. 7 is a photograph of a portion of the same liver from which the image of FIG. 8 was obtained. FIG. 7 depicts the results from a wedged hepatic venogram with an equilibrium phase after injection with a yellow color dye. In the equilibrium phase, infusion and withdrawal parameters were monitored so that no transsinusoidal leakage has occurred. The sample depicted in FIG. 7 confirms that no significant amount of any such leakage has occurred. No leakage of the fluids injected into the subject liver beyond the in vivo closed loop established with the present invention is perceptible in either of FIGS. 7 and 8. Because of this, compositions may be administered according to the present invention, which have not often used in the past, due to adverse side effects, such as those described above for doxorubicin, or due to system toxicity.

The present invention augments the physician's senses by means of a software program capable of tracing the activity of the submicroscopic nonlinear fluid dynamics and a high-resolution, interactive 3-D imaging means to visualize and manipulate the dynamic images.

The effective local delivery of anticancer or other therapeutic agents via the retrograde perfusion delivery device and process is a very promising new treatment modality. Feasibility studies using the new delivery system have yielded remarkable efficiency in the local hepatic delivery of doxorubicin, a widely-used anticancer agent whose use in conventional delivery methods induces life-threatening damage to the heart.

Tissue and blood analysis results from experimental data confirmed that the new system and method of drug delivery proved an astounding ability to deliver therapy to a local site with little or no systemic leakage and negligible effect on the heart—typically 0.07% concentration of doxorubicin in the target region, typically 0.03% in heart tissue, and typically 99% collected in waste blood.

The disclosed system and means controls the delivery of therapy via the retrograde perfusion modality by providing the "right time" monitoring and presentation of a multitude of complex and continually changing variables and interactions occurring at the microscopic and sub-microscopic cellular level beyond human perception.

It should be noted and understood that there can be improvements and modifications made of the present invention described in detail above without departing from the spirit or scope of the invention as set forth in the accompanying claims.

What is claimed is:

1. A computer-implemented method of monitoring retrograde venous perfusion of a tumor in a patient's body, comprising the steps of:

monitoring the positioning of a withdrawal catheter within vasculature of a target vessel in the patient's body near the tumor and an infusion catheter within the vasculature of the target vessel extending beyond the withdrawal catheter and near the tumor;

monitoring the positioning of a venous pressure catheter concentrically disposed between the infusion catheter and the withdrawal catheter forming a closed loop flow path between the positioned infusion catheter and the positioned withdrawal catheter through the target vessel;

monitoring venous pressure in the closed loop flow paths; and monitoring the circulation of a fluid through the closed loop flow path.

2. The computer-implemented method of claim 1, further including the step of: entering data results of at least one of the steps of monitoring into a database.

3. The computer-implemented method of claim 2, wherein the database includes a local database.

4. The computer-implemented method of claim 3, wherein the database includes a central database in communication with the local database.

5. The computer-implemented method of claim 2, further including the step of retrieving from the database available data concerning the patient.

6. The computer-implemented method of claim 2, further including the step of: recalling data from the database during the retrograde perfusion.

7. The computer-implemented method claim 6, further including the step of: displaying the recalled data to the treating physician.

8. The method of claim 1, wherein the fluid in the step of circulating is a saline fluid, and further including the step of: establishing that the closed loop flow path is achieved.

9. The computer-implemented method of claim 8, further including the step of: circulating a dye-containing solution through the closed loop flow path subsequent to the step of establishing.

10. The computer-implemented method of claim 9, further including the step of: forming a visible image of the established closed loop flow path.

11. The computer-implemented method of claim 10, further including the step of: storing data in the database data representing the visible image formed of the established closed loop flow path.

12. The computer-implemented method of claim 8, further including the step of: circulating a therapeutic solution through the closed loop flow path subsequent to the step of establishing.

13. The computer-implemented method of claim 12, wherein the therapeutic solution is a chemotherapeutic agent.

14. The computer-implemented method of claim 13, further including the step of: forming a visible image of the measurable flow of the chemotherapeutic agent through the closed loop flow path.

15. The computer-implemented method of claim 14, further including the step of: storing data in the database representing the flow of the therapeutic agent through the closed loop flow path.

16. The computer-implemented method of claim 13, further including the step of: storing data in the database regarding the treatment of the tumor through circulation of the therapeutic solution.

17. The computer-implemented method of claim 1, further including the steps of: displaying the results of at least one of the steps of monitoring during the retrograde venous perfusion.

18. A data processing system for monitoring retrograde venous perfusion therapy of a tumor in a patient's body as the therapy is occurring, the data processing system comprising:
a processor for performing the steps of: monitoring the positioning of a withdrawal catheter within the vasculature of a target vessel in the patient's body near the tumor and an infusion catheter within the vasculature of the target vessel extending beyond the withdrawal catheter and near the tumor; monitoring the positioning of a venous pressure catheter concentrically disposed between the infusion catheter and the withdrawal catheter, thereby forming a closed loop flow path between the positioned infusion catheter and the positioned withdrawal catheter through the target vessel; monitoring venous pressure in the closed loop flow paths; monitoring the circulation of a fluid through the closed loop flow path; and a data output display for providing the results of monitoring by the processor.

19. A computer program product stored in signal bearing media for causing a data processor to monitor retrograde venous perfusion on therapy of a tumor in a patient's body as the therapy is occurring, the computer program product containing instructions stored in machine-readable code and causing the processor to perform the following steps: monitoring the positioning of a withdrawal catheter within vasculature of a target vessel in the patient's body near the tumor and an infusion catheter within the vasculature of the target vessel extending beyond the withdrawal catheter and near the tumor; monitoring the positioning of a venous pressure catheter concentrically disposed between the infusion catheter and the withdrawal catheter, thereby forming a closed loop flow path between the positioned infusion catheter and the positioned withdrawal catheter through the target vessel; monitoring venous pressure in the closed loop flow paths; and monitoring the circulation of a fluid through the closed loop flow path.

20. A computer-implemented method of monitoring retrograde venous perfusion of a tumor in a patient's body, comprising the steps of:
monitoring the positioning of a withdrawal catheter within the vasculature of a target vessel in the patient's body near the tumor, and monitoring an infusion catheter concentrically disposed within the withdrawal catheter and near the tumor;
monitoring the positioning of a venous pressure catheter concentrically disposed within the withdrawal catheter;
thereby forming one or more closed loop flow paths between the positioned infusion catheter, the positioned withdrawal catheter, and the positioned venous pressure monitoring catheter, through the target vessel;
monitoring venous pressure in the closed loop flow paths; and
monitoring the circulation of a fluid through the closed loop flow paths.

* * * * *